(12) United States Patent
Xu et al.

(10) Patent No.: US 6,337,148 B1
(45) Date of Patent: Jan. 8, 2002

(54) COPPER SOURCE REAGENT COMPOSITIONS, AND METHOD OF MAKING AND USING SAME FOR MICROELECTRONIC DEVICE STRUCTURES

(75) Inventors: Chongying Xu, New Milford; Thomas H. Baum, New Fairfield, both of CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/318,440

(22) Filed: May 25, 1999

(51) Int. Cl.[7] ............................ C07F 1/08; C23C 14/14; C23C 16/06
(52) U.S. Cl. ........................ 428/675; 428/901; 427/252; 556/110; 556/112
(58) Field of Search ................................ 428/675, 901, 428/446, 450; 427/252; 586/110, 112

(56) References Cited

U.S. PATENT DOCUMENTS

| | | | |
|---|---|---|---|
| 5,085,731 A | 2/1992 | Norman et al. | 156/646 |
| 5,098,516 A | 3/1992 | Norman et al. | 156/666 |
| 5,144,049 A | 9/1992 | Norman et al. | 556/12 |
| 5,204,314 A | 4/1993 | Kirlin et al. | 505/1 |
| 5,225,561 A | 7/1993 | Kirlin et al. | 546/256 |
| 5,280,012 A | 1/1994 | Kirlin et al. | 505/1 |
| 5,322,712 A | 6/1994 | Norman et al. | 427/248.1 |
| 5,358,743 A | 10/1994 | Hampden-Smith et al. | 427/282 |
| 5,453,494 A | 9/1995 | Kirlin et al. | 534/15 |
| 5,767,301 A * | 6/1998 | Senzaki et al. | 556/9 |
| 5,817,367 A | 10/1998 | Chun | 427/250 |
| 5,820,664 A | 10/1998 | Gardiner et al. | 106/287.17 |
| 5,840,897 A | 11/1998 | Kirlin et al. | 546/2 |
| 6,099,903 A * | 8/2000 | Kaloyeros et al. | |
| 6,102,993 A * | 8/2000 | Bhandari et al. | |
| 6,110,529 A * | 8/2000 | Gardiner et al. | |

OTHER PUBLICATIONS

U.S. application Ser No. 07/615,303, Brown et al, filed Nov. 19, 1990.
H.K. Shin, et al., "Chemistry of Copper(I) β–Diketonate Complexes. 2. Synthesis, Characterization, and Physical Properties of (β–Diketonato) copper (I) Trimethylphosphine and Bis(trimethylphosphine) Complexes" *Inorg. Chem.* 1992, 31, 424–431 (no month).
A. Jain, et al., "Chemical vapor deposition of copper via disproportionation of hexafluoroacetylacetonato(1,5–cyclooctadiene)cooper(I), (hfac)Cu(1,5,–COD)" *J. Mater. Res.*, 1992, vol. 7, No. 2, 261–264. (no month).
K.M. Chi, et al., "Synthesis and Characterization of (β–Diketonato) copper(I) Alkyne Complexes: Structural Characterization of (Hexfluoroacetylacetonato)(dipenylacetylene)copper(I)" *Inorg. Chem.*, 1991, 30, 4293–4294 (no month).
Nobuyoshi Awaya and Yoshinobu Arita, "Deposition Mechanism of Copper CVD" *Conference Proceedings ULSI–VH 1992 MRS*, 345–354 (no month).

\* cited by examiner

*Primary Examiner*—Deborah Jones
*Assistant Examiner*—Jason Savage
(74) *Attorney, Agent, or Firm*—Margaret M. Chappuis; Steven J. Hultquist

(57) ABSTRACT

Copper precursors useful in liquid delivery CVD for forming a copper-containing material on a substrate. The disclosed copper precursors are particularly useful for metallization of interconnections in semiconductor device structures.

40 Claims, 3 Drawing Sheets

COPPER SOURCE REAGENT COMPOSITIONS, AND METHOD OF MAKING AND USING SAME FOR MICROELECTRONIC DEVICE STRUCTURES

BACKGROUND OF THE INVENTION

1. Field of the Invention

The present invention relates to copper precursor compositions and their synthesis, and to the use of such copper precursor compositions for the fabrication of microelectronic device structures, e.g., in the formation of copper-based interconnects in the manufacture of semiconductor integrated circuits, or in otherwise metallizing or forming copper-containing films on a substrate by metalorganic chemical vapor deposition (MOCVD) utilizing such precursor compositions.

2. Description of the Related Art

The process of fabricating semiconductor integrated circuits generally includes the formation of metal interconnect lines. Such metal interconnect lines often are formed from multiple conductive layers. For example, a thin conductive layer (termed a "barrier layer" in this context) may be formed from a metal, a metal nitride or a metal silicide, with a thicker conductive layer of aluminum, copper or other metal deposited over the barrier layer.

Many semiconductor device manufacturers are adopting copper metallization for use in production of microelectronic chips. Copper interconnects offer chip manufacturers a number of advantages, including enhanced circuit speed, improved performance and reduced electro-migration effects. Any of the one or more metal layers (e.g., bulk layer and/or seed layer) of a semiconductor integrated circuit may be formed utilizing a copper-based film. Furthermore, low resistivity, low contact resistance, and reduced RC time delays make copper particularly desirable for use in the metallization of very large scale integration (VLSI) devices.

In order to prevent detrimental effects caused by the interaction of a copper layer with other portions of the integrated circuit, a barrier layer is typically utilized in conjunction with the copper layers. Any of a wide range of barrier materials may be utilized including materials comprising metals, metal nitrides or metal silicides. Exemplary barrier materials include titanium nitride, titanium suicide, tantalum nitride, tantalum silicide, tungsten nitride, tungsten silicide and silicon doped metal nitrides. After the formation of a barrier layer, the copper is deposited on the barrier layer. The initial copper deposition may function as an electro-chemical or CVD seed layer, e.g., an adhesive, conducting seed layer, followed by electrochemical plating or CVD of copper, for instance to complete the thin-film interconnect. Alternatively, the copper deposition may be employed to fully deposit the desired amount of copper.

For practical applications, the copper CVD precursors for the metallization composition should remain stable at room temperature and should not decompose at the vaporization temperature (e.g., the temperature required to efficiently vaporize the precursor). Concurrently, however, the precursor must decompose at elevated temperature to form high-purity Cu films on the heated substrate surface. The satisfaction of these parameters requires a delicate balance because the difference between the vaporization temperature and the film growth temperature is typically quite small (~100° C.).

A suitable thermal stability can be realized by using bi-dentate neutral Lewis base ligands such as an ene-one. In this manner, the combination of the two coordination sites can be "fine-tuned." Further, chelating complexes usually exhibit better stability than monodentate complexes.

Chemical vapor deposition (CVD) of copper provides uniform coverage for the metallization. Liquid CVD precursors enable direct delivery or liquid injection of the precursors into a CVD vaporizer unit. The accurate and precise delivery rate can be obtained through volumetric metering to achieve reproducible CVD metallization during VLSI device manufacturing.

Currently only a few liquid copper precursors are commercially available. These include (hfac)Cu(MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and VTMS=vinyltrimethylsilane. However, concerns have arisen regarding perfluoro-β-diketonate ligands, such as hfac, because the fluorine can react on the substrate surface forming a thin interface layer of $CuF_2$, leading to poor adhesion and high contact resistances of Cu films on the substrate. Copper CVD precursors with a reduction of fluorine-content or without fluorine are therefore highly desirable. The present invention provides new (β-diketonate)CuL precursors (wherein L is a coordinating ligand in the (β-diketonate)CuL complex) with reduced and/or eliminated fluorine content in the complexes having utility in CVD of Cu thin films.

Furthermore, to achieve a reproducible film growth process, liquid precursors are extremely desirable. To date, only a few (hfac)CuL complexes are liquids that satisfy the requirements for CVD precursors. An organic solution prepared from a solid precursor provides a significant opportunity to increase the precursor availability for various purposes. However, it is well known that the solutions of (hfac)CuL complexes display poor stability. For example, a 50% ether solution of (hfac)Cu(MHY) decomposes in a few days at room temperature while the neat precursor is stable for at least 6 months. Therefore, there is a clear need to continuously develop reliable liquid source materials (neat or in a thermally stable chemical solution) for the CVD of Cu thin films. The present invention provides new stable (hfac)CuL precursors compositions and solutions.

As previously noted, the use of various copper precursors in CVD reactors to create copper interconnects in semiconductor integrated circuits, for example, is well known. U.S. Pat. Nos. 5,085,731; 5,098,516; 5,144,049; and 5,322,712 provide examples; and the references cited in these patents provide additional examples of such precursors. New and useful compositions and processes for the production of copper that improve upon, or provide alternatives to, these known compositions are highly desirable.

Copper CVD processes that are suitable for the large-scale manufacture of integrated circuits are extremely valuable to the electronics industry. Towards these ends, Cu CVD is generally used for two purposes: (1) deposition of a conductive thin-film layer as a plating base ("seed") for electroplating processes; and (2) full-fill deposition of copper interconnects, features and multi-level structures.

There is, therefore, a need in the art for new and improved copper precursors for metallization in the manufacture of integrated circuits and other microelectronic device structures, using techniques such as CVD, plasma-assisted CVD, etc. Further, improved vaporization can lead to greatly improved deposition processes.

It is accordingly an object of the present invention to provide new copper precursors and formulations.

It is another object of the invention to provide methods of forming copper in the manufacturing of integrated circuits and other microelectronic device structures.

It is a further object of the invention to provide metallization technology for forming interconnects and other integrated device structures that overcome the shortcomings and limitations of the prior art, namely robust manufacturing.

It is another object of the invention to provide a method of metallizing or forming copper-containing thin films on a substrate by metalorganic chemical vapor deposition (MOCVD) utilizing such novel copper precursors and solution compositions.

Other objects and advantages of the present invention will be more fully apparent from the ensuing disclosure and appended claims.

SUMMARY OF THE INVENTION

The present invention relates to copper source reagent compositions, and to methods of making, stabilizing and using the same.

In one broad aspect, the present invention relates to novel (β-diketonate)CuL precursors with increased thermal stability, with reduced fluorine content (relative to various corresponding commercial copper source reagents) and having utility for chemical vapor deposition (CVD) of copper thin films (i.e., copper deposited at a thickness of less than about 1000 µm), as well as to methods for making and using such precursors and compositions.

In another aspect, the present invention relates to methods of synthesizing (β-diketonate)CuL complexes, comprised of reacting $Cu_2O$ with corresponding (β-diketonate)H in the presence of the desired Lewis base ligands, L, yielding complexes with increased thermal stability and/or reduced fluorine content as compared to the existing commercial copper MOCVD precursors.

In another embodiment the present invention relates to partially fluorinated or nonfluorinated β-diketonates, such as tfac and tfdac and thd.

In a specific aspect, the present invention provides a CVD process that uses the aforementioned copper precursors, that may alternatively be in the form of neat liquid, as well as solution compositions of solid and liquid precursors of such type, for copper metallization or for forming copper seed layers, e.g., by direct liquid injection and vaporization. Vaporization may be effected by heating, by acoustics, by ultrasound or by nebulization.

The present invention also relates to novel stable (hfac)CuL precursors and to stable solutions for chemical vapor deposition of copper-containing thin films.

Another aspect of the invention relates to a method of forming a plating base "seed" layer on a substrate for subsequent electroplating, comprising deposition on the substrate of a layer of copper-containing material by liquid delivery CVD using a liquid-phase copper precursor, that is thermally stable at liquid delivery process temperatures, to form the layer of copper-containing material as the electrically conductive plating base seed layer.

A still further aspect of the invention relates to a microelectronic device structure comprising a substrate having a chemical vapor deposited copper plating base seed layer on the substrate, wherein the copper plating base seed layer has been formed using a liquid-phase copper precursor that is thermally stable at liquid delivery temperatures (at which the precursor liquid is vaporized to form a corresponding precursor vapor), but which is readily decomposable at chemical vapor deposition condition temperatures, to yield a copper-containing film on the substrate with which the precursor vapor is contacted.

Another aspect of the invention relates to a method of full-fill copper metallization of a microelectronic device structure, comprising liquid delivery chemical vapor deposition of copper metallization on the microelectronic device structure.

In a further aspect, the invention relates to methods of synthesizing (β-diketonate)CuL complexes by reacting $Cu_2O$ with the corresponding (β-diketonate)H in the presence of Lewis base ligand(s), L, yielding complexes having increased thermal stability and/or reduced fluorine content as compared to the existing commercial copper precursors.

In a specific compositional aspect, the invention relates to a (β-diketonate)CuL complex, selected from the group consisting of:

Precursors of Formula I

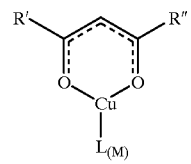

(Formula I)

wherein
M is ½, 1 or 2
R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_3$–$C_6$ fluorocycloalkyl; and
L is a neutral Lewis base ligand, selected from the group consisting of (i) alkenes, (ii) alkynes, (iii) silicon containing ligands, and (iv) sulfur, oxygen and/or nitrogen-containing organic ligands;
(b) precursors of Formula II:

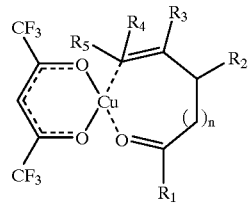

(Formula II)

wherein
$R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and
n is 0, 1, 2, or 3. The bonding mode can be intermolecular or intramolecular.

Another aspect of the invention relates to a method of forming a copper-containing material on a substrate, comprising vaporizing a copper precursor composition to form a precursor vapor, and contacting the precursor vapor with a substrate to form the copper-containing material thereon, wherein the copper precursor composition includes at least one precursor selected from the group consisting of:

(a) precursors of Formula I

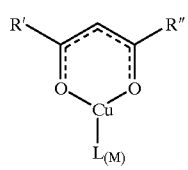

(Formula I)

wherein
M is ½, 1 or 2
R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_3$–$C_6$ fluorocycloalkyl; and
L is a neutral Lewis base ligand, selected from the group consisting of (i) alkenes, (dienes), (ii) alkynes, (iii) silicon containing ligands, and (iv) sulfur, oxygen and/or nitrogen-containing organic ligands;

(b) precursors of Formula II:

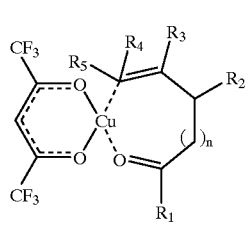

(Formula II)

wherein
$R_1$, $R_2$, $R_3$ $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and
n is 0, 1, 2, or 3.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
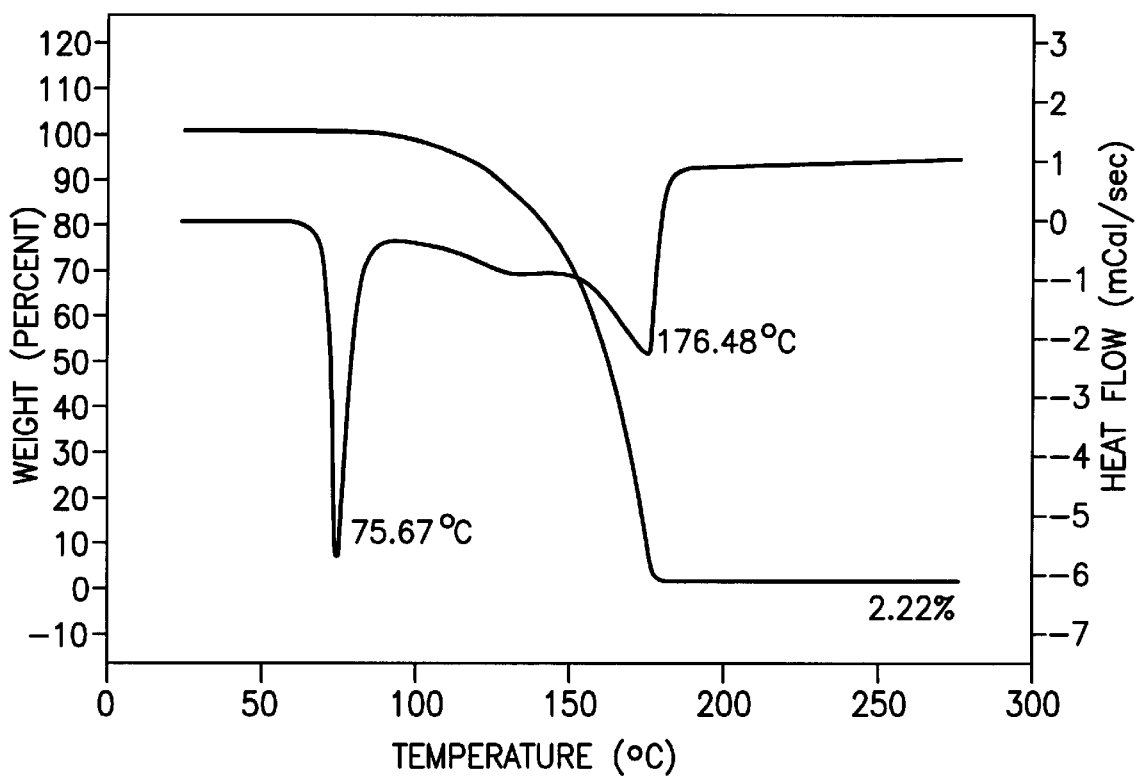
FIG. 1 is a thermal analysis graph for (hfac) Cu(5-hexen-2-one).

The present invention provides new copper precursors for use in the deposition of copper.

In one aspect, the present invention provides novel (β-diketonate)CuL precursors with reduced or eliminated fluorine content, in relation to commercially employed corresponding copper precursors of the prior art. The precursors of the present invention have utility in the chemical vapor deposition formation of copper thin films.

One class of such (β-diketonate precursors has the formula:

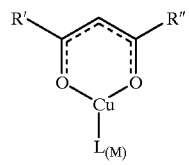

(Formula I)

wherein
M is ½, 1 or 2
R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_3$–$C_6$ fluorocycloalkyl; and
L is a neutral Lewis base ligand, selected from the group consisting of (i) alkenes, (ii) alkynes, (iii) silicon, and (iv) sulfur, oxygen and/or nitrogen-containing organic ligands.

In a preferred aspect, the complexes of Formula I have from 0 to 6 fluorine atoms, with decreasing numbers of fluorine atoms being progressively more preferred. In a most preferred aspect, the complexes have no fluorine atoms.

The complexes of the form (β-diketonate)CuL are readily synthesized by reacting $Cu_2O$ with the corresponding (β-diketonate)H in the presence of the Lewis base ligand, L, as illustrated in the Equation I:

$Cu_2O+2(\beta\text{-diketonate})H+ML \rightarrow 2(\beta\text{-diketonate})CuL_M+H_2O$ (Equation I)

wherein
M is ½, 1 or 2

Another class of copper precursor reagents of the present invention, having improved stability, has the formula (hfac)CuL, i.e.,

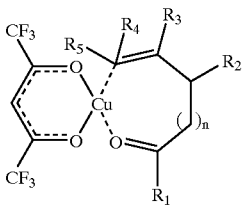

(Formula II)

wherein
$R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and
n is 0, 1, 2, or 3.

The complexes of Formula II are synthesized by reacting $Cu_2O$ and hfacH in the presence of a Lewis base ligand as illustrated in the following equation:

$Cu_2O+2(hfac)H+2\ L \rightarrow 2(hfac)CuL+H_2O$ (Equation II)

The complexes of Formulas I and II may be provided as liquids (which may be used directly) or solids (which may be used in a solution composition formed by dissolving the solid precursor(s) in a suitable solvent medium that provides for long-term stability).

In one embodiment, the present invention provides liquid compositions comprising complexes of Formula I and/or II, wherein L is a neutral Lewis base ligand, such as, ene-one, yne-one, yne-yne, ene-amine and ene-imine, and the complex is either a liquid phase material, or else a solid that has been dissolved in a suitable stabilizing solvent medium. Preferably, the selected solvent has weak donor-capability to stabilize the composition. The solvent for example may be an alkene, such as 1-hexene or cyclohexene. The percentage of the precursor in solution may range from 0.01 to 99.99% by weight, based on the total weight of the solution.

In another embodiment, the present invention provides solvent compositions comprising complexes of Formulas I and/or II, wherein the solvent may for example be selected from hydrocarbons, such as pentane, hexane, heptane, octane etc., or ethers, such as diethyl ether or tetrahydrofuran (THF), or aryls, such as toluene or benzene in combination with alkenes or/and alkynes for enhanced stabilization of the precursor composition. The precursors employed in the solutions may initially be solids, e.g., thermally stable solids that are further stabilized in the solution. The percentage of the precursor in the solution may range from 0.01 to 99.99% by weight, based on the total weight of the solution.

In a specific embodiment, the present invention provides a CVD process that uses one or more of the precursor materials of Formulas I and/or II, e.g., as neat liquid precursors or as a stabilized solution composition, for copper metallization or for the formation of copper seed layers, e.g., via liquid injection or direct vaporization.

In connection with the ensuing discussion, the disclosures of the following United States patents and patent applications are hereby incorporated herein by reference in their entireties:

U.S. patent application Ser. No. 08/835,768 filed Apr. 8, 1997 in the names of Thomas H. Baum, et al.;

U.S. patent application Ser. No. 08/484,654 filed Jun 7, 1995 in the names of Robin A. Gardiner et al.;

U.S. patent application Ser. No. 08/414,504 filed Mar. 31, 1995 in the names of Robin A. Gardiner et al.;

U.S. application Ser. No. 08/280,143 filed Jul. 25, 1994, in the names of Peter S. Kirlin, et al.;

U.S. patent application Ser. No. 07/927,134, filed Aug. 7, 1992 in the same names;

U.S. patent application Ser. No. 07/807,807, filed Dec. 13, 1991 in the names of Peter S. Kirlin, et al., now issued as U.S. Pat. No. 5,204,314;

U.S. application Ser. No. 08/181,800 filed Jan. 15, 1994 in the names of Peter S. Kirlin, et al., and issued as U.S. Pat. No. 5,453,494;

U.S. application Ser. No. 07/918,141 filed Jul. 22, 1992 in the names of Peter S. Kirlin, et al., and issued as U.S. Pat. No. 5,280,012;

U.S. application Ser. No. 07/615,303 filed Nov. 19, 1990;

U.S. application Ser. No. 07/581,631 filed Sep. 12, 1990 in the names of Peter S. Kirlin, et al., and issued as U.S. Pat. No. 5,225,561; and U.S. patent application Ser. No. 07/549,389 filed Jul. 6, 1990 in the names of Peter S. Kirlin, et al.

In general, the copper precursor compositions of the invention may be formulated to comprise, consist of, or consist essentially of any appropriate components herein disclosed, and such copper precursor compositions of the invention may additionally, or alternatively, be formulated to be devoid, or substantially free, of any components taught to be necessary in prior art formulations that are not necessary to the achievement of the objects and purposes of the invention hereunder.

The compositions of the present invention are useful in a number of applications. For example, the compositions may be used in the formation of copper interconnect lines in a semiconductor integrated circuit. To form such integrated circuits, a semiconductor substrate may have a number of dielectric and conductive layers formed on and/or within the substrate.

As used herein, the semiconductor substrate may include a bare substrate or a substrate having any number of layers formed thereon.

A copper-containing layer may typically be formed on the semiconductor substrate for use in a first, second, third, or subsequent metallization layer comprising a multi-level device. Such copper layers are typically used in circuit locations requiring low resistivity and/or high speed circuit paths. As mentioned hereinabove, before a copper layer is formed upon a semiconductor substrate, a barrier layer may be formed on the substrate, with the barrier layer subsequently being overcoated with the copper layer or a copper "seed" layer.

The copper precursor compositions of the invention may be deposited on a wafer or other substrate by use of a CVD system. Metalorganic CVD (MOCVD) systems may be utilized for such purposes, such systems being well known in the semiconductor fabrication art. Preferred MOCVD systems include low-pressure CVD systems.

The compositions of the present invention are not limited in respect of their use with the aforementioned low-pressure CVD deposition tools, however, and other CVD tools, for example PECVD tools, or other deposition tools, may be utilized.

The compositions of the present invention may be delivered to the CVD reactor in a variety of ways. For example, a liquid delivery system may be utilized. Such systems generally include the use of liquid MFCs (mass flow controllers). An exemplary liquid delivery system that may be used is the ADCS Sparta 150 Liquid Delivery System (commercially available from ATMI, Inc., Danbury, Conn.).

Liquid delivery systems generally meter a desired flow rate of the precursor composition in liquid form to the CVD process tool. At the process tool chamber, or upstream thereof, the liquid may be vaporized through use of a vaporizer. Such vaporizers may utilize thermal heating, acoustics, ultrasound and high flow nebulizers. Further descriptions of liquid delivery systems are contained in U.S. Pat. Nos. 5,204,314; 5,362,328; 5,536,323; and 5,711,816, the disclosures of which are hereby expressly incorporated herein by reference in their entireties.

In the practice of the present invention utilizing liquid delivery, the copper precursor species, if of solid form at ambient conditions, may be dissolved or suspended in a compatible solvent medium as more fully described in U.S. Pat. No. 5,820,664 issued Oct. 13, 1998 for "Precursor Compositions For Chemical Vapor Deposition, And Ligand Exchange Resistant Metal-Organic Precursor Solutions Comprising Same," the disclosure of which is hereby incorporated herein in its entirety by reference.

The precursors of the present invention may be deposited using any chemical vapor deposition system known in the art. A preferred liquid delivery MOCVD System is described in U.S. Pat. No. 5,204,314, issued Apr. 20, 1993, for "Method for Delivering an Involatile Reagent in Vapor Form to a CVD Reactor," the disclosure of which is hereby incorporated herein in its entirety by reference.

The use of the compositions disclosed herein is not limited to liquid delivery systems, and any method which adequately delivers the composition to the process tool is satisfactory. Thus, for example, bubbler-based delivery systems may be utilized, but are not preferred. In such systems, an inert carrier gas is bubbled through the precursor composition (typically in liquid form above its melting point). The resulting gas, which is wholly or partially saturated with the vapor of the composition, is provided to the CVD tool.

A wide variety of CVD process conditions may be utilized for chemical vapor deposition employing the compositions of the present invention. Typical liquid delivery MOCVD process conditions may include substrate temperature ranges of 160–300° C., with about 170° C. to about 250° C. being more typical; vaporizer temperature ranges may be from about 50° C. to about 150° C., with about 60° C. to about 100° C. being more typical; pressure ranges are generally from about 0.05 to about 20 Torr (and most preferably from about 0.1 to about 5 Torr), with a range of about 0.2 to about 0.5 Torr being more typical; and inert gas flows of helium or argon of from about 25–750 sccm (and most preferably from about 50 to about 200 sccm), at a temperature approximately the same as the vaporizer. In some cases, a co-reactant may be introduced (i.e., water, alcohol or hydrogen forming gas) to facilitate the film growth process.

The following synthesis examples, including synthesis of new (β-diketonate)CuL complexes, wherein β-diketonate= 1,1,1-trifluoro-5,5-dimethyl-2,4-hexanedionate, (tfdac) 1,1, 1-trifluoro-2,4-hexanedionate, (tfac) or 1,1,1,5,5,5-hexafluoro-2,4-hexanedionate, (hfac); L=dimethyldivinylsilane (DMDVS) or 2-methyl-1-hexen-3-yne (MHY), are representative of specific aspects of the invention and are not intended to limit the scope of the invention or claims hereto. Each of the following general reactions was carried out under a steady flow of nitrogen.

EXAMPLE I

[(tfdac)Cu]$_2$(DMDVS)

A Schlenk flask was charged with 3 g of copper (I) oxide and 3 g of dimethyldivinylsilane (26.7 mmol, 1.05 equivalent on the basis of tfdacH) with 15 mL anhydrous methylene chloride. 1,1,1-trifluoro-5,5-dimethyl-2,4-hexanedione or (tfdac)H (5.0 g, 25 mmol) in 5 mL CH$_2$Cl$_2$ was added dropwise to the magnetically stirred suspension at about 0° C. After the addition, the suspension was stirred for an additional 12 hours at room temperature. The mixture was then filtered through an Al$_2$O$_3$ column, and a light yellow filtrate was collected. Removal of volatiles from the filtrate gave 6.1 g (~85%) yellow liquid. The yellow liquid was characterized by solution NMR. $^1$H NMR (C$_6$D$_6$), δ (ppm) 6.14 (s, 1H, C$\underline{H}$ of tfdac), 4.25–4.55 (m 3H, C$\underline{H}$=CH$_2$), 1.03 (s, 9H, CH$_3$, of t-Bu), 0.17 (s, 6H, CH$_3$). $^{13}$C NMR (C$_6$D$_6$), δ (ppm), 207.8 (s, CH$_3$—C(O)—), 172.2 (q, CF$_3$—$\underline{C}$(O)—), 120.4 (q, $\underline{C}$F$_3$), 102.2 (s, CH=$\underline{C}$H$_2$), 96.7 (s, $\underline{C}$H=CH$_2$), 91.1(s, $\underline{C}$H), 42.9 (s, —$\underline{C}$(CH$_3$)$_3$), 28.2(s, —C($\underline{C}$H$_3$)$_3$), -2.1 (s, Si—($\underline{C}$H$_3$)$_2$).

EXAMPLE II (tfdac)Cu(MHY)

The compound was synthesized as described above, resulting in a white crystalline solid. $^1$H NMR (C$_6$D$_6$), δ(ppm) 6.09 (s, 1H, C$\underline{H}$ of tfdac), 5.65 (m, 1H, H$_a$C$\underline{H}_b$=C of MHY), 5.09 (m, H, H$_a$CH$_b$=C of MHY), 2.24 (q, $\overline{2H}$, C$\underline{H}_2$CH$_3$), 1.82 (m, 3H, $\overline{CH}_3$ of MHY), 1.02 (s, 9H, CH$_3$ of t-Bu), 1.0 (t, 3H, CH$_2$C$\underline{H}_3$ of MHY).

EXAMPLE III

[(tfac)Cu]$_2$(DMDVS)

The compound was synthesized as described above, resulting in a white crystalline solid. $^1$H-NMR (C$_6$D$_6$): 0.17 (s, CH$_3$ of DMDV), 1.68(s, CH$_3$ of tfac), 4.3–4.95 (m, SiCH=CH$_2$ of DMDVS), 5.7 (s, CH of tfac); $^{13}$C-NMR, -2.67 (s), 28.73 (s), 95.35 (s), 103.9, (s) 109.3 (s), 119.8 (q), 171.1 (q).

EXAMPLE IV

[(hfac)Cu]$_2$(DMDVS)

The compound was synthesized as described above, resulting in a white light yellow liquid. NMR (C$_6$D$_6$): $^1$H, 0.04 (s, 6H, CH$_3$), 4.3–4.9 (m, 6H, CH=CH$_2$ of DMDVS), 6.17 (s, 1H, CH of hfac), $^{13}$C, -3.05 (s), 90.2(s), 105.8(s), 111.3(s) 118.3 (q), 178.3(q).MPLE I

EXAMPLE V

Synthesis and Characterization of (hfac)Cu(5-hexen-2-one)

A Schlenk flask was charged with 4.0 g of copper (I) oxide and 2.6 g (27 mmol, 1.1 equivalent on the basis of hfacH) of 5-hexen-2-one with 10 mL anhydrous methylene chloride. 1,1,1,5,5,5-hexafluoroacetylacetone (hfacH) (5.0 g, 24 mmol) in 5 mL CH$_2$Cl$_2$ was added dropwise to the magnetically stirred suspension at about -10° C. After the addition of hfacH, the suspension was stirred for additional 24 hours at room temperature. The mixture was then filtered through a neutral Al$_2$O$_3$ column and a light yellow filtrate was collected. Removal of volatiles of the filtrate gave 6.2 g (~70%) yellow solid. The yellow solid was characterized by solution $^1$H NMR. $^1$H NMR (C$_6$D$_6$), δ(ppm) 6.22 (s, 1H, C$\underline{H}$ of hfac), 4.42 (m=txdxd, 1H, C$\underline{H}$=CH$_2$), 3.56–3.66 (m, 2H, CH=CH$_2$), 1.78 (t, 2H, C$\underline{H}_2$—CH=CH$_2$), 1.60 (m, 2H, —CH$_2$—C$\overline{H}_2$—CH=CH$_2$), 1.56 (s, 3H, C$\underline{H}_3$). $^{13}$C NMR (C$_6$$\overline{D}_6$), δ(ppm), 208 (s, CH$_3$—$\underline{C}$(O)—), 1$\overline{78}$.2 (q, CF$_3$—$\underline{C}$(O)—), 118.6 (q, $\underline{C}$F$_3$), 104.3 (s, =$\underline{C}$H—C(O)), 89.6 (s, $\underline{C}$H$_2$ of hfac), 80.3 (s, =$\underline{C}$H$_2$), 40.6 (s, —$\underline{C}$H$_2$—C(O)), 29.2 (s, —$\underline{C}$H$_2$—CH=) and 27.4 (s, —C(O)—$\underline{C}$H$_3$).

EXAMPLE VI

Preparation of Stable Liquid Composition of (hfac)Cu(5-hexen-2-one)

One gram of (hfac)Cu(5-hexen-2-one) was dissolved in one gram of 1-hexene (approximately 1.8 M). A clear yellow solution was obtained. The solution remained at room temperature for at least 10 weeks without decomposition, indicating that the thermal stability of the solution was very good.Referring now to the drawings, FIG. 1 is a plot of precursor transport (TGA) and melting point (DSC) curves for the (hfac)Cu(5-hexen-2-one) complex of the present invention, having a melting point of about 75° C. This material exhibits superior stability and transport in the temperature range of between about 75° C. and 175° C.

Figure 2:
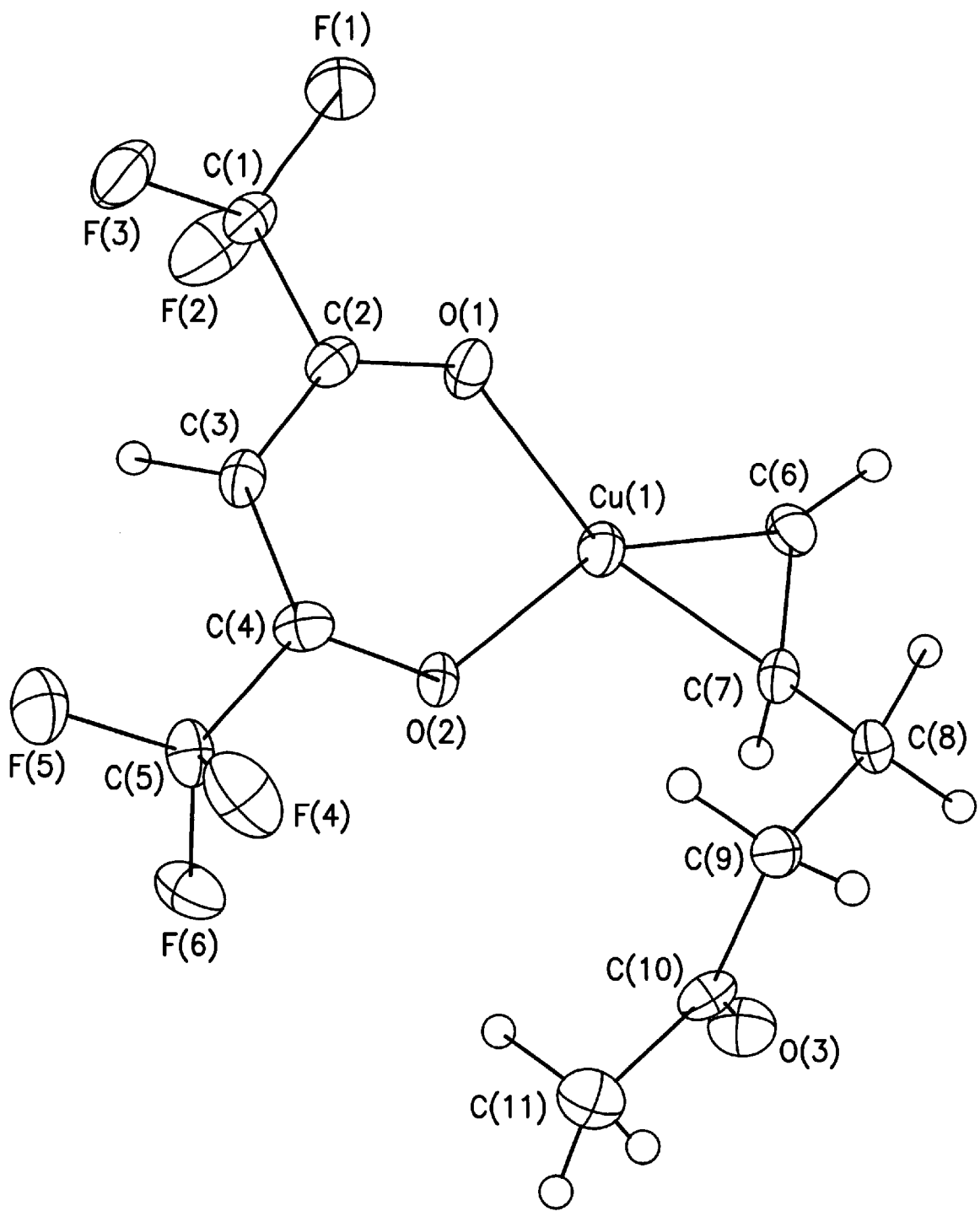
FIG. 2 is an X-ray single crystal diffraction analysis of (hfac)Cu(5-hexen-2-one).

FIG. 2 is an x-ray single crystal diffraction analysis of the (hfac)Cu(5-hexen-2-one) complex of the present invention. The single crystal x-ray diffraction structural determination conclusively shows the (hfac)Cu(5-hexen-2-one) complex of the present invention to be of mononuclear form.

Figure 3:
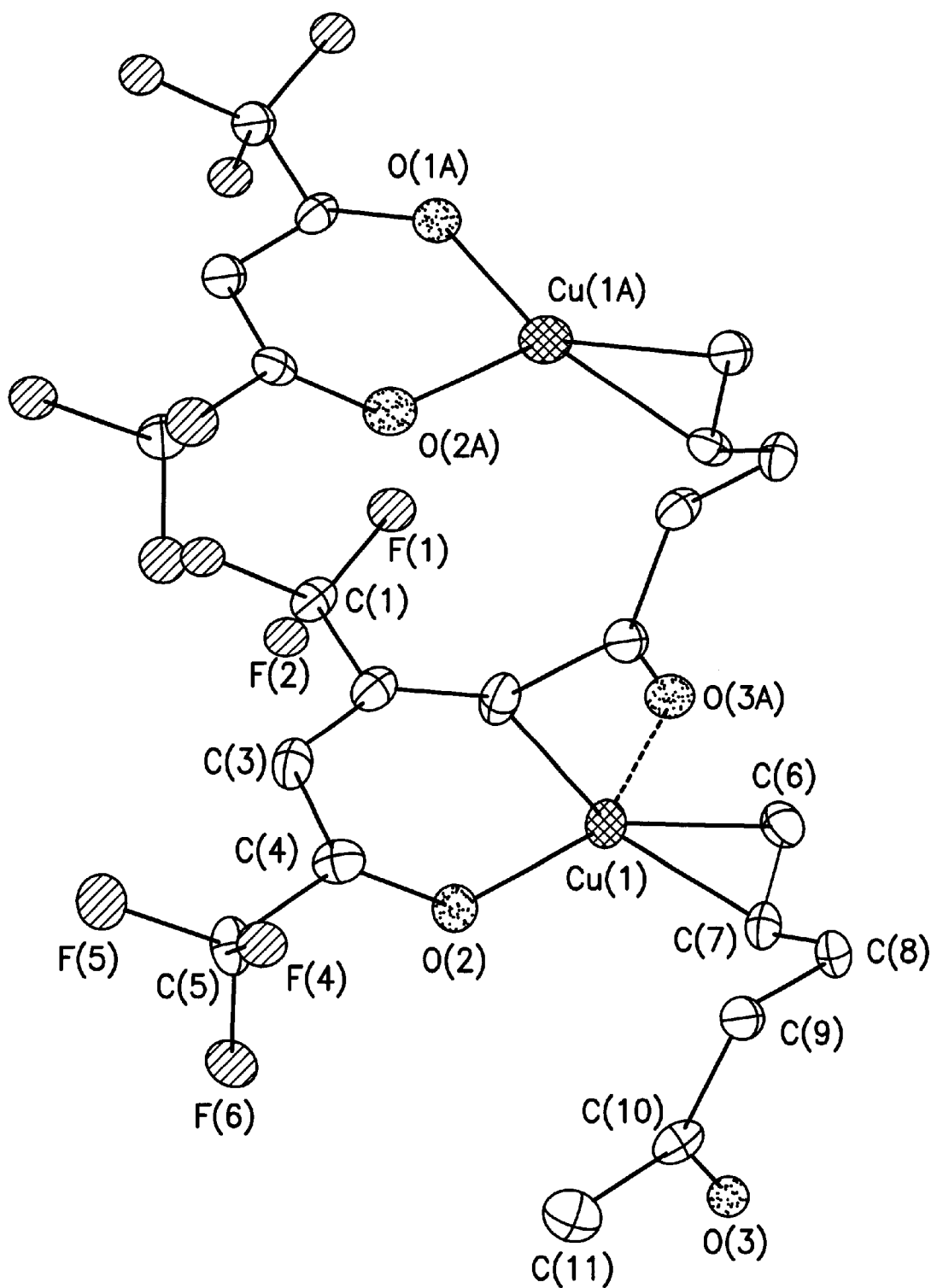
FIG. 3 is an X-ray single crystal diffraction analysis of two (hfac)Cu(5-hexen-2-one) monomers displaying near neighbor interaction.

FIG. 3 further evidences the superior stability of the material in the solid phase to be due in part to interaction between the ketone group from the L group of one molecule of the complex with the Cu atom of a second molecule of the complex. The interaction between the two atoms imparts additional stability to the complex in the solid phase.

Other embodiments of this invention will be readily apparent to those of ordinary skill in the art, based on the disclosure herein. For example, the addition of stabilizers, water, hfac hydrate or other co-reactants may be advantageously employed.

The liquid delivery approach achieves reproducible film growth and uniform deposition rates. A combined liquid delivery and flash vaporization process may be employed, as for example utilizing an LDS300 liquid delivery and vaporizer unit (commercially available from ATMI, Inc., Danbury, Conn.), to enable low volatility materials to be volumetrically delivered, leading to reproducible transport and deposition without thermal decomposition of the precursor. Both of these considerations are essential to providing a commercially acceptable copper MOCVD process.

The deposition of copper thin films with useful electrical properties (low resistivity) and good adhesion to the barrier layer (e.g., formed of TiN or TaN), is also accommodated by the process and precursors of the present invention. The conformality of the deposited film is practically achievable only through CVD techniques, which thereby provide a pathway to the achievement of "full-fill" copper metallization. The liquid delivery approach, including "flash" vaporization and the use of copper precursor chemistry as herein disclosed, enables next-generation device geometries and dimensions to be attained, e.g., a conformal vertical interconnect of 0.13 micron linewidth with 4–8:1 aspect ratio. The conformal deposition of interconnects at these critical dimensions cannot be realized by currently available physical deposition methods. Thus, the approach of the present invention affords a viable pathway to future generation devices, and embodies a substantial advance in the art. Further, improved adhesion and low contact resistances are other improvements over the prior art.

The copper precursors of the invention may be utilized in various CVD processes for copper metallization or the formation of a copper seed layer via either liquid injection or direct vaporization.

The instant invention also enables liquid delivery CVD of copper electroplating base "seed" layers. The use of thermally stable copper precursors, such as the precursors of Formula II of the present invention, provides a distinct advantage for copper CVD, especially for the deposition of the plating base layer. The enhanced thermal stability of this precursor eliminates the need for additives to stabilize the compound. Further, the thermal stability of the precursor allows liquid delivery techniques to be used to achieve reproducible film growth and uniform deposition rates. The combined liquid delivery and enhanced thermal stability allows low volatility materials to be volumetrically delivered, leading to reproducible transport and deposition.

This approach thus produces a conformal, thin-film with good electrical properties and high adhesion to the barrier layer, thereby enabling electroplating technologies to be extended to next-generation device geometries and dimensions, e.g., a conformal plating base with 0.13 μm linewidths and 4–8:1 aspect ratio vias.

While the invention has been described herein with reference to specific features and illustrative embodiments, it will be recognized that the utility of the invention is not thus limited, but rather extends to and encompasses other features, modifications and alternative embodiments, as will readily suggest themselves to those of ordinary skill in the art based on the disclosure and illustrative teachings herein. The claims that follow are therefore to be construed and interpreted, as including all such features, modifications and alternative embodiments within their spirit and scope.

What is claimed is:

1. A copper source reagent composition, comprising at least one copper precursor selected from the group consisting of:

(a) copper complexes of the formula:

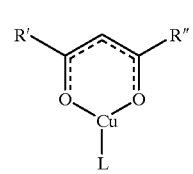

(Formula I)

wherein

R', R", are the same or different and are independently selected from the group consisting of $C_1$–$C_8$ acyclic alkyl, aryl, fluoroaryl, $C_1$–$C_8$ fluoroalkyl, or $C_3$–$C_6$ cycloalkyl, and $C_3$–$C_6$ cycloalkyl, and $C_3$–$C_6$ fluorocycloalkyl; and L is an organic neutral Lewis base ligand, selected from the group consisting of (i) alkenes, (ii) alkynes, (iii) silicon containing ligands , and (iv) sulfur, oxygen and/or nitrogen-containing organic ligands;

with the provisos that when R' and R" are both $CF_3$, L is not 1,5-cyclooctadiene (COD), dimethyl-1,5-cyclooctadiene (DMCOD), vinyltrimethylsilane (VTMS) 2-butyne, 2-pentyne, 2-methyl-1-hexen-3-yne (MHY), or 3-hexyne; and when at least one of R' or R" is $CF_3$ L is not 1,5-cyclooctadiene (COD), vinyltrimethylsilane (VTMS), 2-butyne or 2-pentyne; and (b) copper complexes of the formula:

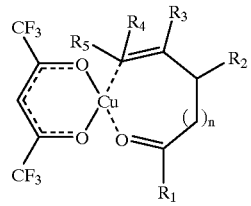

(Formula II)

wherein $R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

2. The composition according to claim 1 wherein the precursor comprises a copper complex of the formula:

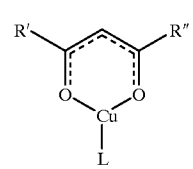

(Formula I)

wherein

R', R", are the same or different and are independently selected from the group consisting of $C_1$–$C_8$ acyclic alkyl, aryl, fluoroaryl, $C_1$–$C_8$ fluoroalkyl, or $C_3$–$C_6$ cycloalkyl, and $C_3$–$C_6$ cycloalkyl, and $C_3$–$C_6$ fluorocycloalkyl; and L is a neutral Lewis base ligand, selected from the group consisting of (i) alkenes, (ii) alkynes, (iii)

silicon containing ligands, and (iv) sulfur, oxygen and/or nitrogen-containing organic ligands;

with the provisos that when R' and R" are both $CF_3$, L is not 1,5-cyclooctadiene (COD), dimethyl-1,5-cyclooctadiene (DMCOD), vinyltrimethylsilane (VTMS), 2-butyne, 2-pentyne 2-methyl-1-hexen-3-yne (MHY), or 3-hexyne; and when at least one of R' or R" is $CF_3$, L is not 1,5-cyclooctadiene (COD), vinyltrimethylsilane (VTMS), 2-butyne or 2-pentyne.

3. The composition according to claim 1 wherein the total number of fluorine atoms is 0 to 6.

4. The composition according to claim 1 wherein the total number of fluorine atoms is 0 to 5.

5. The composition according to claim 1 wherein the total number of fluorine atoms is 0 to 4.

6. The composition according to claim 1 wherein the total number of fluorine atoms is 0 to 3.

7. The composition according to claim 1 wherein the total number of fluorine atoms is 0 to 2.

8. The composition according to claim 1 wherein the total number of fluorine atoms is 1.

9. The composition according to claim 1 wherein the total number of fluorine atoms is 0.

10. The composition according to claim 1 substantially free of fluorine.

11. The composition according to claim 1 wherein the precursor comprises a copper complex of the formula:

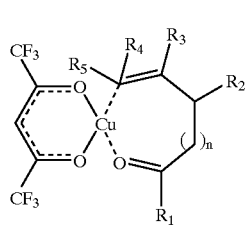

(Formula II)

wherein $R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

12. The composition of claim 1 comprising at least one of said copper complexes and a solvent.

13. The composition of claim 12 wherein the solvent is selected from the group consisting of a hydrocarbon, an aryl, an ether, and a ketone.

14. The composition of claim 12 wherein the solvent is selected from the group consisting of pentane, hexane, heptane and octane.

15. The composition of claim 12 wherein the solvent is selected from the group consisting of diethyl ether and tetrahydrofuran.

16. The composition of claim 12 wherein the solvent is toluene.

17. The composition of claim 12, wherein the solvent is a stabilizing agent.

18. The composition of claim 17 wherein the solvent is selected from the group consisting of 1-hexene, 1-pentene and cyclohexene.

19. The composition of claim 17, wherein the solvent comprises at least one component selected from the group consisting of alkenes and alkynes.

20. The composition of claim 17, wherein the solvent comprises at least one alkyne selected from the group consisting of pentynes, hexynes, heptynes and octynes.

21. The composition of claim 17, wherein the solvent comprises at least one alkyne selected from the group consisting of pentynes, hexynes, heptynes and octynes.

22. The copper source reagent composition according to claim 1, wherein the copper complex is $[(tfdac)Cu]_2$ (DMDVS).

23. The copper source reagent composition according to claim 1, wherein the copper complex is (tfdac)Cu(MHY).

24. The copper source reagent composition according to claim 1, wherein the copper complex is $[(tfac)Cu]_2$ (DMDVS).

25. The copper source reagent composition according to claim 1 further comprising a stabilizing solvent.

26. A method for producing a copper containing layer on a substrate, comprising vaporizing a composition comprising a copper precursor and contacting the copper precursor vapor with the substrate to deposit thereon a copper containing layer, wherein the copper precursor is selected from the group consisting of:

(a) copper complexes having the formula:

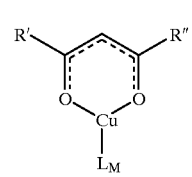

(Formula I)

wherein

M is ½, 1 or 2; R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_{3-6}$ fluorocycloalkyl; and L is an organic neutral Lewis base ligand, selected from the group consisting of (i) alkenes, (ii) alkynes, (iii) silicon-containing ligands, and (iv) sulfur, oxygen and/or nitrogen -containing organic ligands;

with the provisos that when R' and R" are both $CF_3$, L is not 1,5-cyclooctadiene (COD), dimethyl-1,5-cyclooctadiene (DMCOD), vinyltrimethylsilane (VTMS), 2-butyne, 2-pentyne, 2-methyl-1-hexen-3-yne (MHY), or 3-hexyne; and when at least one of R' or R" is $CF_3$, L is not 1,5-cyclooctadiene (COD), vinyltrimethylsilane (VTMS), 2-butyne or 2-pentyne; and (b) copper complexes having the formula:

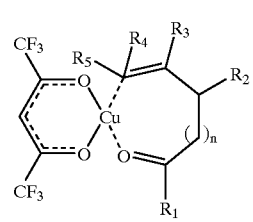

(Formula II)

wherein $R_1$, $R_2$, $R_3$, R4 and $R_5$ may be the same or different and are selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

27. The method of claim 26 wherein deposition of copper occurs during manufacture of an integrated circuit.

28. The method of claim 26, wherein the composition is vaporized through use of a liquid delivery system.

29. An integrated circuit made using the method of claim 26.

30. Copper made by a process comprising chemical vapor depositing copper on a substrate from a copper precursor selected from the group consisting of:

(a) copper complexes having the formula:

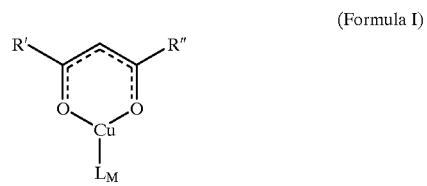

(Formula I)

wherein

M is ½, 1 or 2; R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_3$–$C_6$ fluorocycloalkyl; and L is an organic neutral Lewis base ligand, selected from the group consisting of (i) alkenes, (ii) alkynes, (iii) silicon-containing ligands, and (iv) sulfur, oxygen and/or nitrogen-containing organic ligands; with the provisos that when R' and R" are both $CF_3$, L is not 1,5-cyclooctadiene (COD), dimethyl-1,5-cyclooctadiene (DMCOD), vinyltrimethylsilane (VTMS), 2-butyne, 2-pentyne, 2-methyl-1-hexen-3-yne (MHY), or 3-hexyne; and when at least one of R' or R" is $CF_3$, L is not 1,5-cyclooctadiene (COD), vinyltrimethylsilane (VTMS), 2-butyne or 2-pentyne; and (b) copper complexes having the formula:

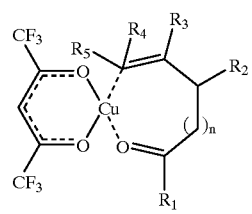

wherein $R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

31. A method of forming a seed layer on a substrate by liquid injection or direct vaporization including vaporizing a composition comprising a copper complex and a solvent, to produce a copper precursor vapor, and contacting said precursor vapor with the substrate to deposit thereon said seed layer, wherein said copper complex is selected from the group consisting of:

(a) copper complexes having the formula:

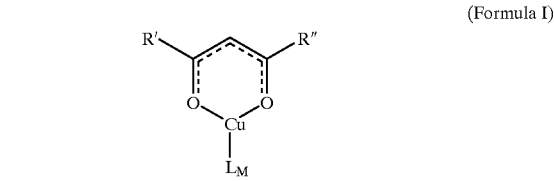

(Formula I)

wherein

M is ½, 1 or 2; R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloallyl, and $C_3$–$C_6$ fluorocycloalkyl; and L is an organic neutral Lewis base ligand, selected from the group consisting of (i) alkenes, (ii) alkynes, (iii) silicon-containing ligands, and (iv) sulfur, oxygen and/or nitrogen-containing organic ligands; and (b) copper complexes having the formula:

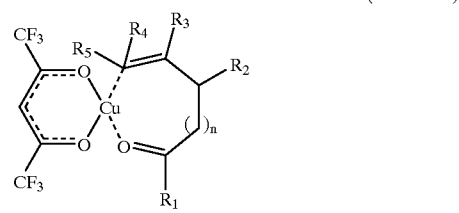

(Formula II)

wherein $R_1$, $R_2$, $R_3$, $R_4$ and $R_5$, may be the same or different and are selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

32. A method of making a complex having the formula:

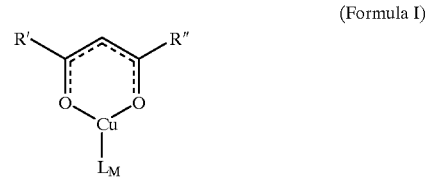

(Formula I)

wherein

M is ½, 1 or 2; R' and R" are the same or different and are independently selected from the group consisting of $C_1$–$C_8$ acyclic alkyl, aryl, fluoroaryl, $C_1$–$C_8$ fluoroalkyl, $C_3$–$C_6$ cycloalkyl, and $C_3$–$C_6$ fluorocycloalkyl; and (Formula II)

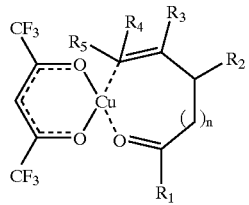

wherein
R$_1$, R$_2$, R$_3$, R$_4$ and R$_5$ may be the same or different and are independently selected from the group consisting of H, aryl, fluoroaryl, C$_1$–C$_8$ acyclic alkyl, C$_1$–C$_8$ fluoroalkyl, or C$_3$–C$_6$ cycloalkyl, and n is 0, 1, 2, or 3.

33. A method of making a complex having the formula:

(Formula II)

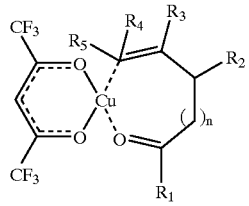

wherein
R$_1$, R$_2$, R$_3$, R$_4$ and R$_5$ may be the same or different and are independently selected from the group consisting of H, aryl, fluoroaryl, C$_1$–C$_8$ acyclic alkyl, C$_1$–C$_8$ fluoroalkyl, or C$_3$–C$_6$ cycloalkyl, and
n is 0, 1, 2, or 3;
said method comprising:

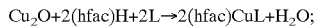

Cu$_2$O+2(hfac)H+2L→2(hfac)CuL+H$_2$O;

wherein L is as defined above.

34. The method of claim 33 utilizing a copper complex of formula (II).

35. A method of forming a plating base seed layer on a substrate, comprising depositing on said substrate a layer of copper-containing material by liquid delivery CVD using a liquid-phase copper precursor comprising at least one solvent or stabilizing agent and at least one complex selected from the group consisting of:

(a) copper complexes having the formula:

(Formula I)

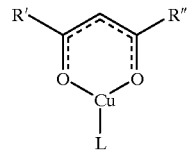

wherein
R' and R" are the same or different and are independently selected from the group consisting of C$_1$–C$_8$ acyclic alkyl, aryl, fluoroaryl, C$_1$–C$_8$ fluoroalkyl, C$_3$–C$_6$ cycloalkyl, and C3–C6 fluorocycloalkyl; and
L is a neutral Lewis base ligand, selected from the group consisting of (i) alkenes, (ii) alkynes, (iii) silicon, and (iv) sulfur, oxygen and/or nitrogen-containing organic ligands; and (b) copper complexes having the formula:

(Formula II)

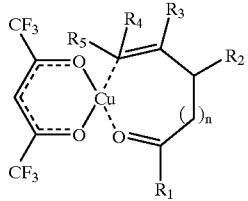

wherein
R$_1$, R$_2$, R$_3$ and R$_4$ may be the same or different and are selected from the group consisting of H, aryl, fluoroaryl, C$_1$–C$_8$ open-chain alkyl, C$_1$–C$_8$ fluoroalkyl, or C$_3$–C$_6$ cycloalyl, and
n is 0, 1, 2, or 3.

36. The method according to claim 35 utilizing a copper complex of formula I.

37. The method of claim 35, further comprising electroplating a conductive material on the plating base seed layer.

38. A microelectronic device structure comprising a substrate having a chemical vapor deposited copper plating base seed layer on the substrate, wherein the copper plating base seed layer has been formed by liquid injection or direct vaporization using a liquid-phase copper precursor comprising at least one solvent or stabilizing agent and at least one copper complex that is thermally stable at vaporization temperatures and is substantially free of fluorine wherein said copper precursor comprises at least one copper complex selected from the group consisting of:

(a) copper complexes of the formula:

(Formula I)

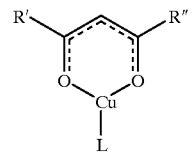

wherein
R', R", are the same or different and are independently selected from the group consisting of C$_1$–C$_8$ acrylic alkyl, aryl, fluoroaryl, C$_1$–C$_8$ fluoroalkyl, or C$_3$–C$_6$ cycloalkyl, and C$_3$–C$_6$ cycloalkyl, and C$_3$–C$_6$ fluorocycloalkyl; and
L is a neutral Lewis base ligand, selected from the group consisting of (i) alkenes, (ii) alkynes, (iii) silicon containing ligands, and (iv) sulfur, oxygen and/or nitrogen-containing organic ligands; and (b) copper complexes of the formula:

(Formula II)

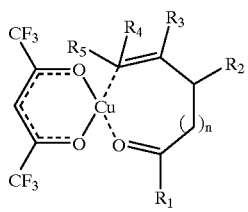

wherein $R_1$, $R_2$, $R_3$, $R_4$ and $R_5$ may be the same or different and are independently selected from the group consisting of H, aryl, fluoroaryl, $C_1$–$C_8$ acyclic alkyl, $C_1$–$C_8$ fluoroalkyl, or $C_3$–$C_6$ cycloalkyl, and n is 0, 1, 2, or 3.

39. The microelectronic device structure of claim 38, further comprising an electroplated metal on the copper plating base seed layer.

40. A copper source reagent composition, comprising at least one copper precursor and at least one stabilizing solvent, wherein the copper precursor is selected from the group consisting of:

(a) copper complexes of the formula:

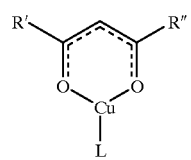

(Formula I)

wherein

R', R", are the same or different and are independently selected from the group consisting of $C_1$–$C_8$ acyclic alkyl, aryl, fluoroaryl, $C_1$–$C_8$ fluoroalkyl, or $C_3$–$C_6$ cycloalkyl, and $C_3$–$C_6$ cycloalkyl, and $C_3$–$C_6$ fluorocycloalkyl; and L is an organic neutral Lewis base ligand, selected from the group consisting of (i) alkenes, (ii) alkynes, (iii) silicon containing ligands, and (iv) sulfur, oxygen and/or nitrogen-containing organic ligands; and (b) copper complexes of the formula:

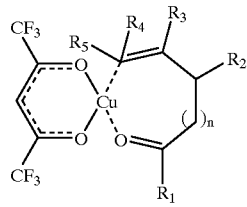

(Formula II)

wherein $R_1$, $R_2$, $R_3$, $R_4$ and $R_5$ may be the same or different and are independently selected from the group consisting of H, aryl, fluoroaryl, $C_1$–$C_8$ acyclic alky, $C_1$–$C_8$ fluoroalkyl, or $C_3$–$C_6$ cycloalkyl, and n is 0, 1, 2, or 3.

* * * * *